United States Patent [19]

Dahms

[11] Patent Number: 4,924,005
[45] Date of Patent: May 8, 1990

[54] BISMALEIMIDE RESINS

[75] Inventor: Ronald H. Dahms, Springfield, Mass.

[73] Assignee: Monsanto Company, St. Louis, Mo.

[21] Appl. No.: 944,157

[22] Filed: Dec. 18, 1986

[51] Int. Cl.$^5$ .......................................... C07D 209/56
[52] U.S. Cl. .................................................. 548/521
[58] Field of Search ...................................... 548/521

[56] References Cited

U.S. PATENT DOCUMENTS 4,460,783  7/1984  Nishikawa et al. ................ 548/549

OTHER PUBLICATIONS

James A. Harvey, Richard P. Chartoff, and John M. Butler, "New Aromatic-Ether Bismaleimide Matrix Resins", *ANTEC*'86, pp. 1311–1315.

*Primary Examiner*—Mukund J. Shah
*Assistant Examiner*—C. L. Cseh
*Attorney, Agent, or Firm*—R. B. Blance; T. E. Kelley; W. J. Farrington

[57] ABSTRACT

Substantially insoluble bismaleimide compositions consisting essentially of bismaleimides of the formula

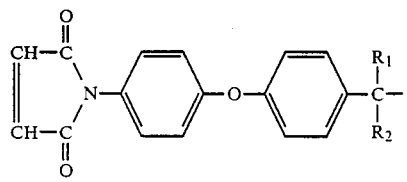

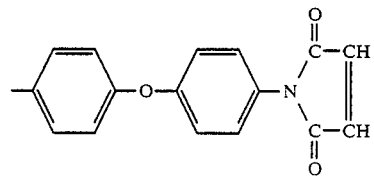

where $R_1$ and $R_2$ are independently hydrogen, methyl, ethyl or halogenated methyl. The phenyl groups may be substituted. The compositions, having a solubility in acetone of less than about 5% by wt., are useful as melt processable resins for high temperature resistant laminates.

4 Claims, No Drawings

BISMALEIMIDE RESINS

Disclosed herein are inventions relating to bismaleimide resins.

BACKGROUND OF THE INVENTION

Bisimide resins, e.g. bismaleimide resins, are advantageously used in providing resin matrix composites, e.g. glass or carbon fiber reinforced laminates, to achieve enhanced properties such as greater thermal stability and lower moisture sensitivity than is possible with other composites, e.g. composites based on epoxy or other resins. A common bisimide, i.e. bis(4-maleimidophenyl)methane, exhibits a cure temperature close to its melt temperature. Its use in commercial manufacture of laminates is facilitated by melt point depression through the addition of methylene dianiline (which exhibits undesirable toxicity).

Nishikawa, et al., disclose in U.S. Pat. No. 4,460,783 certain aromatic ether bismaleimide compounds such as bis(maleimidophenoxyphenyl) propane and the like. Nishikawa, et al., disclose that such ether imides are highly soluble in desirable solvents such as acetone, toluene, methyl ethyl ketone and the like. See also Harvey et al in "New Aromatic-Ether Bismaleimide Matrix Resins", *ANTEC '86*, page 1311.

It has been discovered that the solubility of such aromatic ether bismaleimides is dependent on the presence of a considerable amount of acid group-containing precursor, i.e. having terminal amic acid groups not converted to the terminal imide group. Such acidic precursor material advantageously renders the bisimide soluble. However the terminal acid groups will tend to liberate water from ring closing imidization during cure of such resin. Such water will be vaporized during normal curing conditions and may tend to generate voids or blisters in fabricated articles such as laminates. Such water liberation is tolerable in some fabrication practices that can accommodate liberated water. However, in other applications it is especially desirable that bisimide resins cure with minimal liberation of water. An object of this invention is to provide such aromatic ether bismaleimide resin comprising substantially low levels of imide precursor acid groups.

SUMMARY OF THE INVENTION

This invention provides substantially insoluble bismaleimide compositions consisting essentially of bismaleimides of the formula

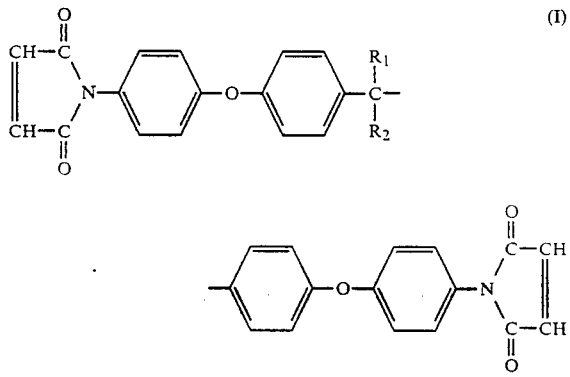

where $R_1$ and $R_2$ is independently hydrogen, a methyl group, an ethyl group or a halogenated methyl group, e.g. a trifluoro methyl group. The phenyl groups may be unsubstituted or substituted, e.g. with lower alkyl groups, lower alkoxy groups halogens or other common substitutents. The compositions of this invention will desirably exhibit a solubility in common organic solvents such as acetone less than about 5 percent by weight at 20° C. To achieve such insolubility the compositions will have only minor amounts of amic acid precursor (i.e. the bis amic acid and the mono amic acid precursor) such that the composition exhibits a molar ratio of maleimide groups to maleamic acid groups of greater than 20 to 1. In some applications where minimal water liberation during cure is desired, such compositions may preferably have a molar ratio of maleimide groups to maleamic acid groups of at least about 30 to 1.

The compositions of this invention are obtained by separating materials consisting essentially of the bismaleimide from the imidization reaction product resulting from ring closing dehydration of amic acid precursors. Such imidization reaction is effected to varying degrees of completion resulting generally in a product comprising a mixture of the bismaleimide, the bisamic acid precursor and the half reacted intermediate compound having both maleimide and maleamic acid terminal groups. The preparation of such mixture is disclosed in U.S. Pat. No. 4,460,783, incorporated herein by reference. The ring closing dehydration of the bismaleamic acid precursor is preferably carried out in the presence of an acid anhydride to assist dehydration, tertiary amine such as triethylamine to assist in ring closing, and a catalyst such as nickel acetate.

Purification of the bismaleimide can be achieved by dissolving the imidization reaction product in a solvent such as acetone at levels of up to about 50 percent by weight or higher, say at least about 70 percent by weight. It has been found that the bismaleimide will preferentially precipitate from such solutions. Selective precipitation may occur within a short period of time or may take several hours to commence. Factors influencing the rate and quantity of bismaleimide precipitation are generally known to those skilled in the art and include the initial solids concentration, degree of mixing, degree of cooling and the like. It has generally been found that substantial quantities of the bismaleimide can be separated from a solution upon sitting at room temperature for about 24 hours. Although the bismaleimide is recovered as a precipitate from solution, it is often possible to provide such bismaleimide temporarily in solution, e.g. by vigorous mixing, heating or other known solubilizing techniques. The term "substantially insoluble" as used herein is intended to characterize bismaleimide material that does not form stable solutions. Accordingly, it is a further characteristic of the composition of this invention that when at least about 40 parts of the composition is mixed with acetone at room temperature to provide 100 parts of solution, that substantial quantities, e.g. at least about 25% of said composition is separated from said solution after 24 hours.

Bismaleimide compositions of this invention are substantially insoluble in common organic solvents such as acetone, toluene, methyl ethyl ketone and the like. They do exhibit solubility, however, in aprotic solvents such as N-methyl pyrrolidone, dimethyl acetamide, dimethyl formamide, dimethyl sulfoxide, and the like. Accordingly, the bismaleimide compositions of this invention can be used to provide bismaleimide resin matrix composites by saturating fiber reinforcement materials, such as glass or carbon filament or cloth, woven or nonwoven, with a solution of such bismaleimide compounds or with molten bismaleimide compound. Such bismaleimide compounds are cured by heating at temperatures of e.g. 100°–300° C.

The following disclosure is provided to illustrate specific embodiments and aspects of the invention but does not imply any limitation of the scope of the invention.

EXAMPLE 1

This example illustrates the preparation of a bismaleimide composition according to this invention, i.e. bis(-maleimidophenoxyphenyl) propane.

351 grams of maleic anhydride and 1,012 grams of acetone were heated to reflux temperature (about 63° C.) in a 5-liter reaction flask. A solution of 693 grams of 2,2-bis[4-(4-amino-phenoxy)phenyl]propane in 1,350 grams of acetone was metered into the refluxing solution over a period of 40 minutes. The reaction mixture was held at 30 minutes at reflux temperature to provide essentially 100 percent complete conversion to the diamic acid of 2,2-bis4-(4-amino-phenoxy)phenyl]propane precipitated as a yellow powder.

The following materials were added to the suspension of diamic acid in refluxing acetone: 495 grams of acetic anhydride, 3.375 grams of nickel acetate tetrahydrate, and 58.5 grams of triethylamine. The suspension was maintained at reflux temperature for about two hours then cooled to 50° C. The resulting clear solution was stirred into cold water yielding a precipitated yellow powder which was washed with water to remove solubles, filtered and dried in an air oven at 60° C. to constant weight. Analysis by high pressure liquid chromatography indicated that the powder comprised about 76 percent of the bismaleimide of 2,2-bis[4-(4-aminophenoxy)phenyl]propane and about 5 percent of the diamic acid; the balance of the powder is believed to be the half imidized intermediate having both maleimide and maleamic acid terminal groups.

The maleimide maleamic acid mixture was dissolved in acetone at room temperature (75% solids/25% acetone, by weight). After standing overnight (about 16 hours), about 50% of the solids precipitated from the acetone solution. The acetone-insoluble material was washed with acetone and dried. Analysis by high pressure liquid chromatography indicated that the acetone-insoluble material was about 93% bismaleimide; its solubility in acetone, methyl ethyl ketone and a toluene/acetone solution (50/50) was less than 5% by weight.

The acetone-insoluble bismaleimide will remain in a molten state at about 175° C. for greater than about 4 hours. Upon heating to about 250° C., the acetone insoluble bismaleimide cures to a solid thermosetting resin.

While specific embodiments of the invention have been described, it should be apparent to those skilled in the art that various modifications thereof can be made without departing from the true spirit and scope of the invention. Accordingly, it is intended that the following claims cover all such modifications within the inventive concept.

What is claimed is:

1. A substantially insoluble composition consisting essentially of bismaleimides of the formula

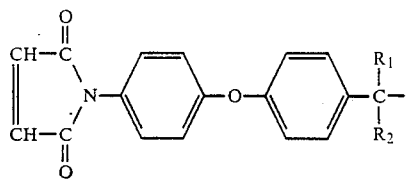

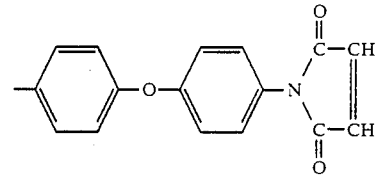

where $R_1$ and $R_2$ is independently a hydrogen, methyl ethyl, or halogenated methyl group wherein said composition exhibits a solubility in acetone at 20° C. of less than about 5 percent by weight.

2. The composition of claim 1 consisting essentially of the bismaleimides and minor amounts of maleamic acid-containing precursors of said bismaleimides wherein said composition has molar ratio of maleimide groups to precursor maleamic acid groups of greater than about 20 to 1.

3. The composition of claim 2 wherein the said ratio is at least about 30 to 1.

4. The composition of claim 2 wherein said bismaleimide is bis(maleimidophenoxyphenyl) propane.

* * * * *